United States Patent

Stanley

(10) Patent No.: US 9,504,552 B2
(45) Date of Patent: Nov. 29, 2016

(54) HEMODIALYSIS GRAFT

(71) Applicant: Cook Medical Technologies LLC, Bloomington, IN (US)

(72) Inventor: Cleon Stanley, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 523 days.

(21) Appl. No.: 13/690,547

(22) Filed: Nov. 30, 2012

(65) Prior Publication Data

US 2013/0138139 A1    May 30, 2013

Related U.S. Application Data

(60) Provisional application No. 61/565,192, filed on Nov. 30, 2011.

(51) Int. Cl.
| | | |
|---|---|---|
| A61F 2/01 | (2006.01) | |
| A61F 2/95 | (2013.01) | |
| A61F 2/06 | (2013.01) | |
| A61M 1/36 | (2006.01) | |
| A61B 17/50 | (2006.01) | |
| A61B 17/3207 | (2006.01) | |
| A61M 39/02 | (2006.01) | |

(52) U.S. Cl.
CPC .................. *A61F 2/01* (2013.01); *A61B 17/50* (2013.01); *A61F 2/06* (2013.01); *A61F 2/95* (2013.01); *A61M 1/3655* (2013.01); *A61B 2017/320741* (2013.01); *A61M 2039/0258* (2013.01)

(58) Field of Classification Search
USPC ............................................................ 604/8
See application file for complete search history.

(56) References Cited

U.S. PATENT DOCUMENTS

| | | | |
|---|---|---|---|
| 2,616,422 A | 11/1952 | Jones | |
| 3,132,062 A | 5/1964 | Lang et al. | |
| 3,500,819 A | 3/1970 | Silverman | |
| 4,892,539 A | 1/1990 | Koch | |
| 5,246,452 A | 9/1993 | Sinnott | |
| 5,571,169 A | 11/1996 | Plaia et al. | |
| 5,628,788 A | 5/1997 | Pinchuk | |
| 5,876,445 A * | 3/1999 | Andersen | A61F 2/90 623/23.7 |
| 6,019,788 A * | 2/2000 | Butters | A61B 17/064 604/8 |
| 6,156,064 A | 12/2000 | Chouinard | |
| 6,245,011 B1 * | 6/2001 | Dudda | A61B 17/320016 600/104 |
| 6,409,750 B1 * | 6/2002 | Hyodoh | A61F 2/07 623/1.1 |
| 7,166,099 B2 | 1/2007 | Devens, Jr. | |
| 7,182,755 B2 | 2/2007 | Tal | |
| 7,762,977 B2 * | 7/2010 | Porter | A61B 17/11 604/507 |
| 7,794,473 B2 * | 9/2010 | Tessmer | A61F 2/01 606/200 |
| 8,372,109 B2 * | 2/2013 | Tessmer | A61F 2/01 606/200 |
| 8,628,556 B2 * | 1/2014 | Tessmer | A61F 2/01 606/200 |

(Continued)

*Primary Examiner* — Adam Marcetich
*Assistant Examiner* — Guy K Townsend
(74) *Attorney, Agent, or Firm* — Brinks Gilson & Lione

(57) ABSTRACT

A graft is used to interconnect two vessels, such as an artery and a vein for hemodialysis. The graft includes a body having first and second ends, and a wall to define a passageway formed in the body. The wall includes a plurality of tubular layers, such as a first layer and one or more second layers disposed radially inward relative to the first layer. Each second layer has first and second ends that can be enclosable. The second layer is removable from the graft body from within the passageway of the graft body after clot formation. A grasper can be used to attach with at least one of the ends of the second layer. In response to withdrawal of the grasper, the corresponding end of the second layer gathers radially inward away from a layer adjacent to the second layer.

20 Claims, 3 Drawing Sheets

(56) References Cited

U.S. PATENT DOCUMENTS

| | | | | |
|---|---|---|---|---|
| 8,684,960 B2* | 4/2014 | Batiste | ............... | A61M 1/3653 600/36 |
| 8,715,316 B1* | 5/2014 | Janardhan | ............... | A61F 2/01 606/200 |
| 8,715,317 B1* | 5/2014 | Janardhan | ............... | A61F 2/01 606/200 |
| 8,721,677 B1* | 5/2014 | Janardhan | ............... | A61F 2/01 606/200 |
| 8,728,116 B1* | 5/2014 | Janardhan | ............... | A61F 2/01 606/200 |
| 8,728,117 B1* | 5/2014 | Janardhan | ............... | A61F 2/01 606/200 |
| 8,733,618 B1* | 5/2014 | Janardhan | ............... | A61F 2/01 156/60 |
| 8,735,777 B1* | 5/2014 | Janardhan | ............... | A61F 2/01 110/230 |
| 8,784,446 B1* | 7/2014 | Janardhan | ............... | A61F 2/01 606/200 |
| 8,789,452 B1* | 7/2014 | Janardhan | ............... | A61F 2/01 228/262.31 |
| 8,790,365 B1* | 7/2014 | Janardhan | ............... | A61F 2/01 606/200 |
| 8,795,330 B1* | 8/2014 | Janardhan | ............... | A61F 2/01 606/200 |
| 8,803,030 B1* | 8/2014 | Janardhan | ............... | A61F 2/01 219/121.84 |
| 8,813,625 B1* | 8/2014 | Janardhan | ............... | A61F 2/01 623/1.15 |
| 8,816,247 B1* | 8/2014 | Janardhan | ............... | A61F 2/01 219/121.71 |
| 8,828,045 B1* | 9/2014 | Janardhan | ............... | A61F 2/01 606/200 |
| 8,845,678 B1* | 9/2014 | Janardhan | ............... | A61F 2/01 606/159 |
| 8,845,679 B1* | 9/2014 | Janardhan | ............... | A61F 2/01 606/200 |
| 8,852,227 B1* | 10/2014 | Janardhan | ............... | A61F 2/01 606/200 |
| 8,859,934 B1* | 10/2014 | Janardhan | ............... | A61F 2/01 137/563 |
| 8,863,631 B1* | 10/2014 | Janardhan | ............... | A61F 2/01 623/1.53 |
| 8,866,049 B1* | 10/2014 | Janardhan | ............... | A61F 2/01 219/388 |
| 8,869,670 B1* | 10/2014 | Janardhan | ............... | A61F 2/01 623/1.53 |
| 8,904,914 B2* | 12/2014 | Janardhan | ............... | A61F 2/01 228/256 |
| 8,910,555 B2* | 12/2014 | Janardhan | ............... | A61F 2/01 228/47.1 |
| 2003/0040771 A1* | 2/2003 | Hyodoh | ............... | A61F 2/90 606/200 |
| 2003/0167031 A1* | 9/2003 | Odland | ............... | A61M 1/1678 604/8 |
| 2003/0176884 A1 | 9/2003 | Berrada et al. | | |
| 2003/0204168 A1* | 10/2003 | Bosma | ............... | A61B 17/06166 604/103.02 |
| 2004/0220682 A1* | 11/2004 | Levine | ............... | A61F 5/0076 623/23.65 |
| 2005/0182463 A1* | 8/2005 | Hunter | ............... | A61K 45/06 607/115 |
| 2006/0161139 A1* | 7/2006 | Levine | ............... | A61F 5/0079 606/1 |
| 2007/0083271 A1* | 4/2007 | Levine | ............... | A61B 17/0401 623/23.64 |
| 2007/0191931 A1 | 8/2007 | Weber et al. | | |
| 2007/0249986 A1* | 10/2007 | Smego | ............... | A61M 1/3653 604/8 |
| 2008/0027534 A1* | 1/2008 | Edwin | ............... | A61L 27/16 623/1.44 |
| 2008/0039878 A1* | 2/2008 | Williams | ............... | A61B 17/1114 606/153 |
| 2008/0140012 A1 | 6/2008 | Binford | | |
| 2010/0106235 A1 | 4/2010 | Kariniemi et al. | | |
| 2010/0199448 A1* | 8/2010 | Vazales | ............... | A61B 1/126 15/104.05 |
| 2010/0249815 A1 | 9/2010 | Jantzen et al. | | |
| 2011/0046713 A1* | 2/2011 | Cully | ............... | A61F 2/07 623/1.13 |
| 2011/0137428 A1* | 6/2011 | Terliuc | ............... | A61F 5/0089 623/23.64 |
| 2011/0245665 A1* | 10/2011 | Nentwick | ............... | A61M 1/285 600/433 |
| 2011/0264104 A1* | 10/2011 | Naoum | ............... | A61M 1/3655 606/108 |
| 2013/0138139 A1* | 5/2013 | Stanley | ............... | A61F 2/01 606/200 |
| 2014/0018721 A1* | 1/2014 | Gage | ............... | A61M 1/3655 604/8 |
| 2014/0257165 A1* | 9/2014 | Shechtman | ............... | A61M 25/0116 604/8 |

* cited by examiner

HEMODIALYSIS GRAFT

This application claims the benefit under 35 U.S.C. §119(e) of U.S. Provisional Application No. 61/565,192, filed Nov. 30, 2011, which is hereby incorporated by reference herein.

BACKGROUND

The present disclosure relates generally to medical devices. More particularly, it relates to hemodialysis grafts configured for removal of thrombosed regions of the graft.

Hemodialysis includes the use of a dialyzer to clean wastes from blood when a patient's kidneys fail to do so. Also included is a hemodialysis graft, which is connected between an artery and a vein of a patient, preferably in patient's arm. The hemodialysis graft provides a convenient inlet on the artery side for blood requiring dialysis filtration processing, and the outlet is located on the vein side for return of dialysis treated blood from the dialyzer. Regardless of where it is placed, the function of the hemodialysis graft is to facilitate withdrawal of blood from the patient for treatment in a dialyzer and for returning the treated blood to the patient.

Thrombosis, or blood clot formation, is the most common cause of hemodialysis graft failure after a period of time due to stenosis caused by the high rate of blood flow through the graft and repetitive injury at the venous anastomosis. The location of the stenosis is most commonly found at the graft/vein anastomosis, but can also be found along the wall of the graft. A narrowing at this area causes a slow down or obstruction of blood flow, resulting in the formation of the thrombus within the graft. The underlying stenosis, regardless of location, must be corrected in order to avoid recurrence of the thrombus. Typically, patients must have these stenosed regions of the graft widened periodically in order to continue hemodialysis processing through the graft. Furthermore, it is conventional to surgically declot the graft or to install a new graft at a different location. Graft declotting and replacement are surgical procedures, which mean that the patient must undergo repeated surgeries simply to assure blood flow through the graft is adequate to facilitate hemodialysis.

With respect to graft declotting, there are at least three primary interventional radiology methods for percutaneous thrombolysis: Thrombolytic (rolkinase, stereptokinase, Tissue plasminogen activator (TPA, r-TPA), and other) infusion, pulse-spray pharmacomechanical thrombolysis, and pure mechanical thrombolysis. A summary of these various methods can be found in U.S. Pat. No. 7,182,755, which is incorporated herein by reference to its entirety. Despite some advantages, traditional percutaneous thrombolysis often exhibit significant drawbacks. For example, some methods use large devices (8-French or more), which can perform poorly in curved vessels, limiting their use in hemodialysis grafts. Further, residual adherent clot is a considerable problem with some of these methods, and many devices do not remove the macerated clot, which then may be embolized into the lungs.

Thus, what are needed are a hemodialysis graft and a method of use thereof that are configured to minimize graft declotting methods to the implanted graft. It is also desirable to lengthen the period of implantation of the hemodialysis graft, thereby delaying the surgical introduction of replacement grafts.

SUMMARY

Accordingly, a graft, a system, and method of use there are provided herein to address at least some of the shortcomings of the prior art. The graft can be used to interconnect a first body vessel and a second body vessel such as, e.g., for hemodialysis. The graft wall includes a first outer layer and a second inner layer. In order to remove a clot from the graft, the second inner layer is removable from the first outer layer. The inventions herein may also include any other aspect described below in the written description or in the attached drawings and any combinations thereof.

BRIEF DESCRIPTIONS OF THE DRAWINGS

DETAILED DESCRIPTION OF THE DRAWINGS AND THE PRESENTLY PREFERRED EMBODIMENTS

Figure 1:
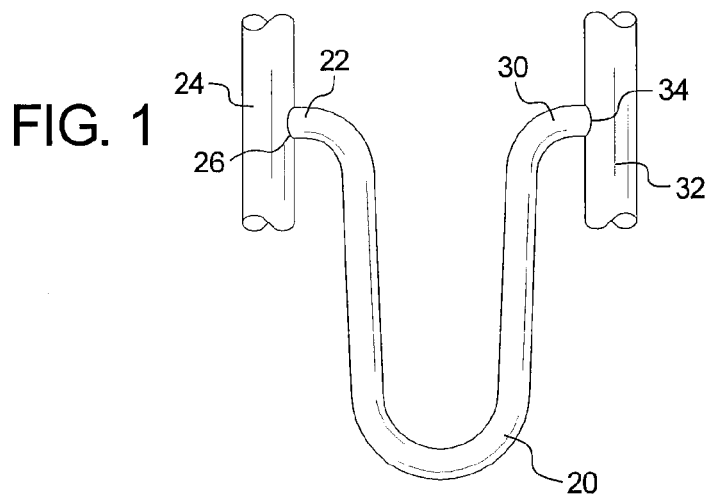
FIG. 1 illustrates a graft interconnected between a first vessel and a second vessel.

For the purposes of promoting an understanding of the principles of the present disclosure, reference will now be made to the embodiments illustrated in the drawings, and specific language will be used to describe the same. Throughout the specification, when referring to a medical device, or a portion of a medical device, the terms "distal" and "distally" shall denote a position, direction, or orientation that is generally towards, or in the direction of, the patient when the device is in use. The terms "proximal" and "proximally" shall denote a position, direction, or orientation that is generally away from the patient, or closer to the operator, during use of the device. It is understood that like-referenced numerals are used throughout the Figures to designate similar components.

A graft that is described herein can be useful for shunting vessels, ducts, or other bodily structures that define lumens or passageways of the body, with the term "body vessel" used in the specification to describe these structures in general. The graft can be used to interconnect two vessels, such as an artery (the inlet side) and a vein (the outlet side), for treatment such as hemodialysis. The wall of the graft can include an outer layer and a plurality of removable inner layers. The innermost inner layer is typically the location where the clot forms, and preferably is formed at the graft/vein anastomosis or outlet side of the fluid subsequent to being treated. The narrowing due to the clot formation causes a slow down or obstruction of blood flow, resulting in the formation of the thrombus within the graft. The removal of the innermost inner layer while the graft is surgically interconnected with the vessels can treat the underlying stenosis, regardless of location, in order to avoid recurrence of the thrombus. To that end, the first and second ends of the removable inner layer can be cinched with the aid of a grasping retrieval device. After cinching both ends of the removable inner layer, a sack is formed to contain the clot and preferably prevent any fragments of the clot from leaving the sack. The sack can then be removed from the graft with the aid of the grasping retrieval devices still coupled to the ends. After removal of the thrombosed inner layer, the remaining innermost inner layer of the graft provides a declotted inner surface. Thus, while the graft is surgically interconnected between two vessels, subsequent inner layers can be independently removed from the graft to control clot formation along the graft. Thus, the graft and the method of use thereof can minimize graft declotting to lengthen the period of implantation of the graft so the surgical introduction of replacement grafts can be delayed.

Figure 2:
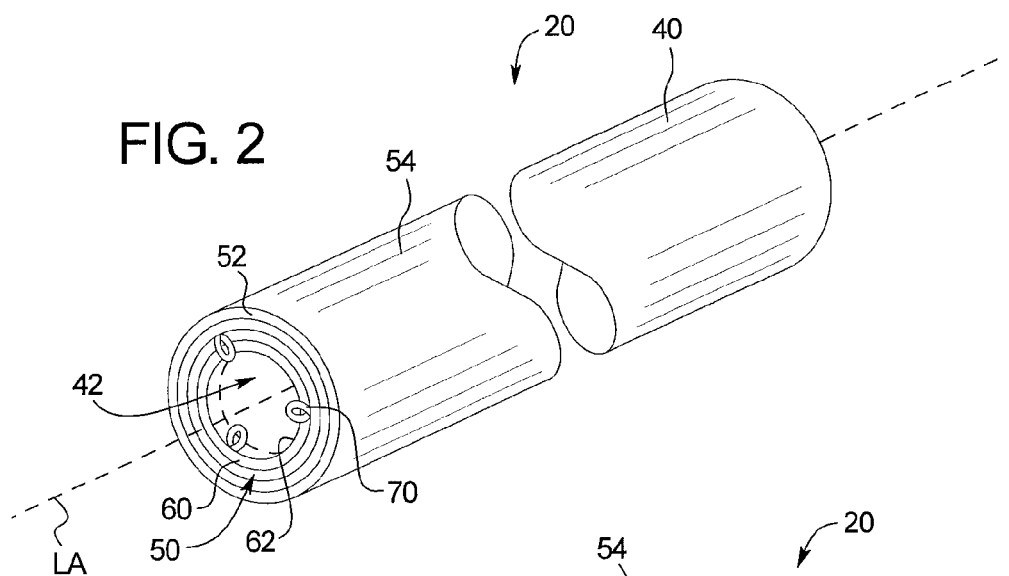
FIG. 2 is a perspective view of one example of a graft.
Figure 3:
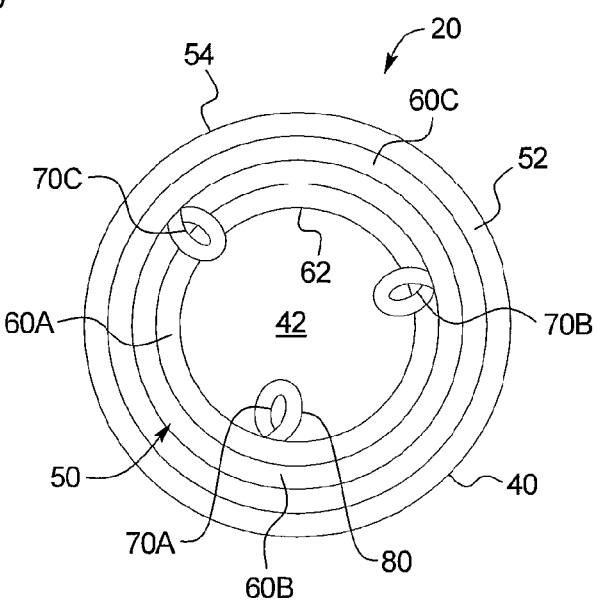
FIG. 3 is an end view of the graft of FIG. 2.

FIG. 1 depicts one example of a graft 20 implanted in the body of a patient, such as for use in hemodialysis. A first, inlet graft end 22 of the graft 20 is surgically coupled to a first body vessel 24, such as an artery, to define an arterial anastomosis 26. This side can be the inlet side where untreated fluid or blood is removed from the body for treatment at an external treatment unit, such as a dialyzer. A second, outlet graft end 30 of the graft 20, opposite the first end, is surgically coupled to a second body vessel 32, such as a vein to define a venous anastomosis 34. This side can be the outlet side where treated fluid or blood is introduced to the body subsequent to treatment at the external treatment unit. In FIGS. 2-3, the graft 20 comprises a tubular graft body 40 having a longitudinal passageway 42 formed therein about the longitudinal axis LA to allow the passage of fluid, such as blood, between the first and second body vessels 24, 32. The graft 20 can be configured to fit a circular, elliptical, marquis-shaped, or other known shaped anastomosis from the first body vessel 24 to the second body vessel 32. Straight, curved, U-shaped, or other known configured grafts are available for a variety of connections, depending upon the position of the desired graft. Nevertheless, the working portion of the graft is preferably tubular, which may have a variety of shapes and/or a variety of luminal diameters throughout the length of the graft.

The wall 50 of the graft body 40 can be composed of multiple tubular layers. Each layer includes a first end associated with the first graft end 22, a second end associated with the second graft end 30, and outer and inner surfaces extending between the ends thereof. For example, the first layer 52, or outermost layer, has an outer surface 54 that generally defines the outer surface of the graft 20 and an inner surface. In one example, the graft body includes an elongated length of hollow polymer tubing. The tubing can have a uniform diameter throughout or can have a variable luminal diameter extending between the first layer ends. One non-limiting example of the first layer 52 includes polytetrafluoroethylene (PTFE). However, it is contemplated that the first layer 52 can be made from a wide variety of biocompatible materials, such as silicone, polyurethane, Dacron, or other known materials used for grafts having acceptable physical characteristics of suitable flexibility and kink resistance.

Disposed radially inward in a coaxial relationship from the first layer 52 can be one or more second layers 60 (shown as layers 60A, 60B, 60C in FIG. 3), or inner layers, which preferably is an abutting relationship with the adjacent outer layer such that no gap therebetween exists. The innermost second layer 60 can be extracted, dissolved, biodegraded, or otherwise controllably removed prior to clot formation along its inner surface from becoming an adverse risk to the patient. The first layer 52 may completely or at least partially overlie the second layer 60. The second layer 60 has an outer surface coupled to a confronting inner surface of the adjacent outer layer, which can be another second layer or the fist layer. The inner surface 62 of the innermost second layer defines the passageway 42 of the graft 20. The inner surface of the other second layers, if employed, is coupled to the confronting outer surface of the adjacent outer layer. FIGS. 2-3 illustrate three second layers 60A-60C, although more or less second layers may be provided as appreciated by those skilled in the art. One non-limiting example of the second layer 60 includes PTFE. However, it is contemplated that the second layer 60 can be made from a wide variety of biocompatible materials, such as silicone, polyurethane, Dacron, or other known materials used for grafts having acceptable physical characteristics of suitable flexibility and kink resistance.

Although the first and second layers 52, 60 may be made from the same material, the first and second layers 52, 60 may also be made from different materials. For example, the first layer 52 may be made from a material that is thicker and/or stronger than the individual second layers 60. Each individual second layer 60 may also be made from a material that is more elastic and/or flexible than the first layer 52. The first and second layers 52, 60 may also have a non-circular cross-section if desired. For example, the cross-section of the first and second layers 52, 60 may have straight sides, which may be advantageous for bonding the layers together. The cross-section may also be oval or oblong, which may be useful to improve blood flow. The longitudinal cross-section of the first and second layers 52, 60 also need not be straight, for example in the case of a straight cylinder. If desired, the longitudinal cross-section may have flared openings at the ends 22, 30 that are larger than the passageway of the central portion of the graft 20. This may be useful to better access the flexible members 72. The first layer 52 may also be reinforced if desired to make the first layer more rigid relative to the second layers 60. For example, the first layer 52 may have integral or bonded ribs extending from the exterior of the first layer 52 in the form of circular or inclined rings or may have a polymer or metal coiled or braided reinforcement.

Figure 4:
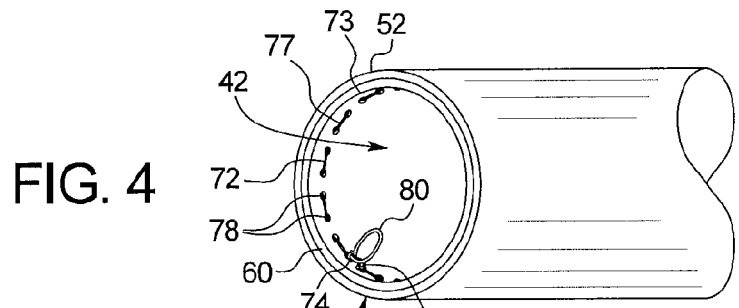
FIG. 4 is a perspective view of an end of a graft, depicting a release system.

As previously described, each second layer can be removed from the graft consecutively at different periods of time depending on the degree of clot formation present on the innermost second layer. After clot formation, the second layer can be removed in a manner to minimize the amount of clot fragments from remaining in the body vessels. In one example, the second layer 60 comprises a release system 70 to facilitate its mechanical removal from the graft 20, and in particular, from the adjacent outer layer. In FIG. 4, the release system 70 includes a first flexible member 72 that is threaded through a series of first end openings 78 formed in the second layer along the first second layer end 73 of the second layer 60 associated with the first graft end 22. A second flexible member (not shown) can be provided at the opposite end of the graft, and attached in a similar manner as the first flexible member 72. Although the term "flexible member" is discussed herein, "flexible member" is not meant to be limiting, as it is understood the flexible member may comprise one or more biocompatible metals or polymers in the form of strands, wires, cords, fibers, yarns, filaments, cables, threads, or the like, such that such terms may be used interchangeably. It is contemplated that the second layer end may have sagging portions to form the release system to allow the grasping retrieval device to directly couple to the second layer instead of the flexible member.

Figure 5:
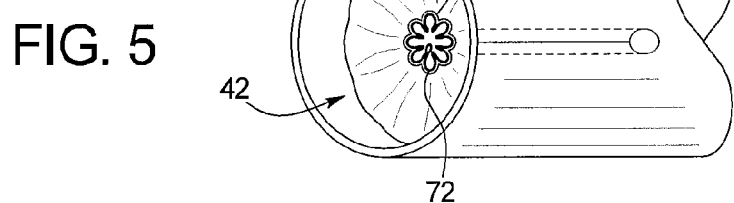
FIG. 5 is a perspective view of the end of the graft of FIG. 4, depicting removal of a second inner layer.

In FIG. 5, tension applied to the flexible member, shown as the first flexible member 72, can gather or cinch the respective end 73 of the second layer 60 radially inward like a purse string. Continuous retraction of the flexible member from within the passageway 42 of the graft 20 can pull the first second layer end 73 of the second layer 60 away from the adjacent outer layer, shown as the first layer 52. The flexible members at the other end of the second layer can be cinched in a similar manner to enclose the other end. This can enclose both of the second layer ends in a manner to prevent clot fragments from escaping from the enclosed ends, thereby forming a sack (as shown in FIG. 7D) to contain the clot during its removal from the body. Subsequent to at least one of the second layer ends being cinched, the second layer 60 is capable of being pulled entirely away from the adjacent outer layer and removed from the body from within the passageway 42 of the graft 20.

In one example, the flexible member 72 has a first end 74, a second end 76, and an intermediate body 77 therebetween. The openings 78 formed in the second layer can be oriented to align along the same circumferential region, zigzag, or other pattern along the second layer. The intermediate body 77 of the flexible member 72 is sized to pass through the respective end openings 78, whereas the first and second flexible member ends 74, 76 are configured not to pass through the openings 78. In one example, the first flexible member end 74 can include a looped segment 80. The looped segment 80 can be a separate member that is coupled to the flexible member. This arrangement may be advantageous when a property such as tensile strength or a shape is desired in the looped segment that is different than found in the flexible member. In one example, the looped segment 80 may be integral with the flexible member and formed by a process of looping the end of the flexible member and attaching the end of the flexible member to itself, with applying an adhesive, thermally bonding, welding, soldering, or using other attachment mechanism know in the art. The second end 76 can be an enlarged end that is sized larger the respective end opening 80.

In another example, the entire flexible member, or in the alternative the looped segment, can be formed of a radiopaque material to permit fluoroscopic visualization of the location of the flexible member or looped segment during the procedure. Such radiopaque materials include metal wires, such as gold, platinum, tantalum, titanium, tungsten, metal-coated polymer fibers, or polymer composite fiber matrices, such as described in U.S. Patent App. Publ. 2007/0172526, which is incorporated herein by reference in its entirety.

A grasping retrieval device as described below can be used by the end user in conjunction with the looped segment to facilitate cinching of the ends of the second layer prior to the graft being removed from the graft body. Thus, as the looped segment 80 is retracted radially inward along the second layer end, the intermediate body 77 is moved relative to the end openings 78, while the enlarged second flexible member end 76 is prevented from moving relative to the end openings 78, thereby causing the second layer end to gather radially inward toward the axis of the graft. To this end, the release system for each second layer, shown as release systems 70A, 70B, 70C in FIG. 3 as the looped segments 80, can be circumferentially offset from one another in order to prevent inadvertent coupling between the grasping retrieval device and a second layer which is not the innermost one.

Figure 6:
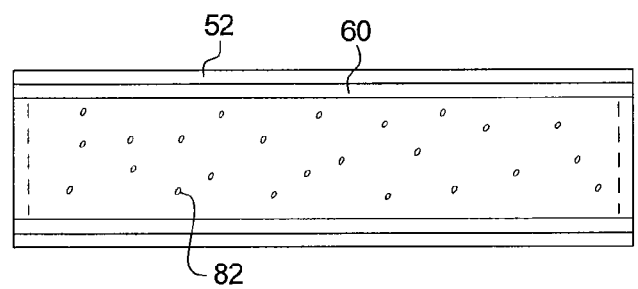
FIG. 6 illustrates an example attachment mechanism between a first outer layer and a second inner layer of a graft.

In one example, each second layer 60 can be attached to the adjacent outer layer in a manner to prevent sagging or from being pulled away by fluid flow, while at the same time allowing the second layer to be pulled from the adjacent outer layer without tearing the adjacent outer layer when desired by the end user. FIG. 6 depicts one example attachment. An adhesive 82 can be applied at several spots, which can be in the form of dots as shown or strips, along the surface of at least one of the layers. The number and size of adhesive spots will be dependent on the strength of the adhesive and the desired retraction strength. It is contemplated that instead of a separate adhesive, the attachment spots can be formed by spot welding to thermally bond the layers at a series of attachment welds. In another example, the attached spots can be formed by tufts comprising suture ties by a method known by those skilled in the art. In yet another example, the adhesive can be a thin continuous layer, instead of or in combination with the spots, disposed between the respective adjacent layers.

To make the graft, the first of the second layers can be placed on a mandril and an adhesive can be applied to the outside surface of the first of the second layers by dipping, spraying, or an applicator capable of dot placement or strip placement. The second layer already has the release system provided at the ends thereof. Before curing, the next outer layer, which can be the second of the second layers or the outer first layer, having a luminal diameter sized at least as large as the outer diameter of the first of the second layers, can be fitted over the first of the second layers that is still on mandril. The adhesive can then be cured to bond the layers together. When a second of the second layers is applied over the first of the second layers, an adhesive can be applied in a similar manner to the outside surface thereof before placement of an additional second layer. The next second layer can be rotated in a manner to circumferentially offset its release system from the adjacent second layer. When all of the second layers are applied, an adhesive can be applied in a similar manner to the outside surface of the outermost second layer before placement of the final outer first layer over the subassembly of the second layers.

Figure 7A:
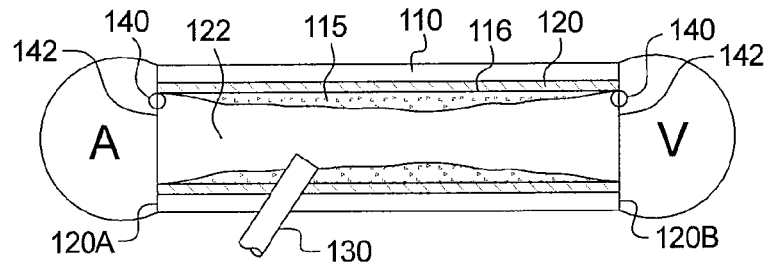
FIGS. 7A-7F illustrate an example method of removal of a second inner layer from a graft interconnected between a first vessel and a second vessel.
Figure 7B:
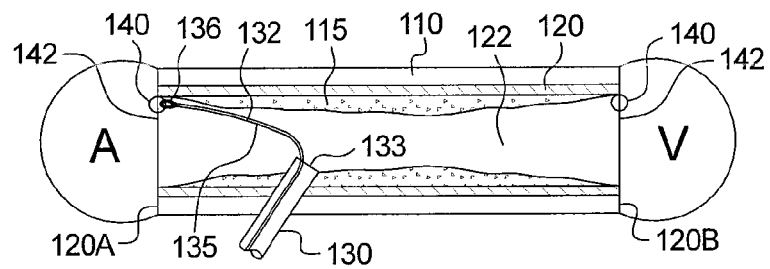
Figure 7C:
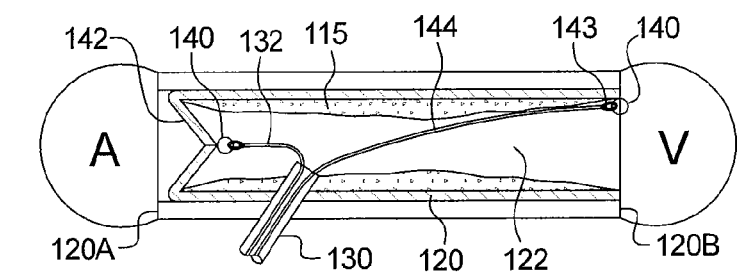
Figure 7D:
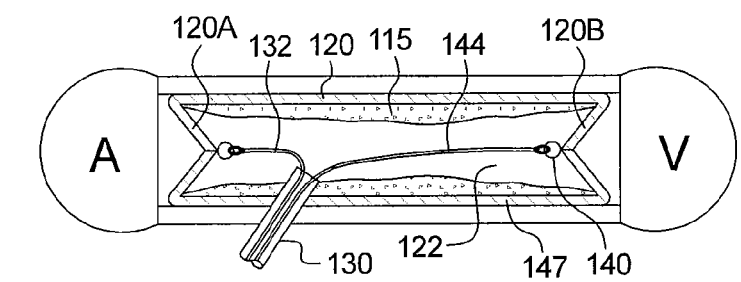

FIGS. 7A-7F illustrate a method of removing the innermost second layer. In FIG. 7A, a graft 110, such as the graft 20, is shown surgically interconnected between a first vessel A and a second vessel V. A clot 115 is shown formed along the inner wall 116 of the innermost second layer 120. Access can be gained within the passageway 122 of the graft 110. For example, an access catheter 130 can be inserted through the wall of the graft 110 using a conventional Seldinger technique with a guidewire. The vessels can be clamped with a hemostat or otherwise prevented from allowing blood to pass through.

In FIG. 7B, a grasping retrieval device 132 is translated through the access catheter 130 and is extendable beyond the distal end opening 133 of the access catheter 130. The grasping retrieval device 132 can be any device that is capable of attaching to the flexible member or the ends of the second layer 120. In one example, the grasping retrieval device 132 includes an elongated shaft 135 and a mechanical grasper head 136 at the distal end of the elongated shaft 135. The elongated shaft 135 can comprise a polymer or metal body or a body formed from a sheath construction. Such sheath construction is described in U.S. Pat. Nos. 5,380,304 and 6,939,337, each of which is incorporated herein by reference in its entirety. It can be desirable for the shaft 135 to exhibit suitable pushability, torqueability, and retractability. The grasper head 136 can be a hook member or a clamping member. In one example, the grasper head 136 is configured to engage with the looped segment 140 of the flexible member 142 at a first end 120A of the second layer 120.

In FIG. 7C, the grasper head 143 of a second grasper device 144, similar to the first grasper device 132 in its configuration, is configured to engage with the looped segment 140 of the flexible member 142 at a second end 120B of the second layer 120. The first grasper device 132 can be retracted within the access catheter 130 to cinch the first end 120A of the second layer and enclose the first end region of the second layer from the adjacent outer layer. In FIG. 7D, the second grasper device 144 can be retracted within the access catheter 130 to cinch the second end 120B of the second layer and enclose the second end region of the second layer from the adjacent outer layer, thereby forming a sack 147 to contain the clot during removal of the sack 147. The enclosing steps can occur simultaneously or in sequence as appreciated by those skilled in the art. Enclosing or otherwise cinching the ends of the second layer before removal thereof can prevent clot fragments from remaining in the body after removal of the sack 147.

Figure 7E:
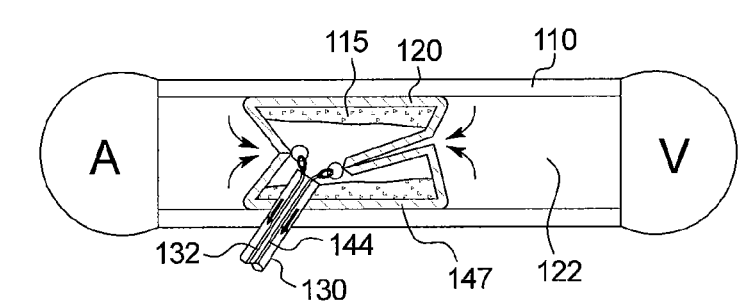
Figure 7F:
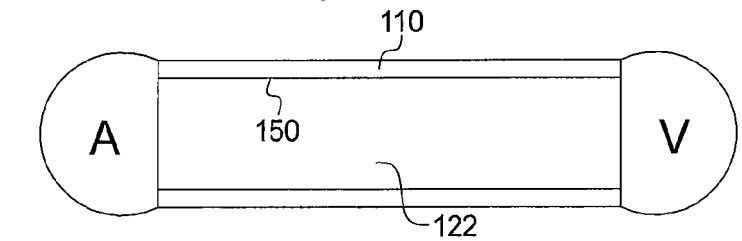

According to FIG. 7E, the grasper retrieval devices 132, 144 can be further retracted within the access catheter so that the enclosed ends of the second layer sack 147 are inverted and urged into the distal end opening of the access catheter 130. The sack 147 formed by the innermost second layer, which included the clot formation, is completely removed from the graft 110. FIG. 7F shows that the consecutive innermost layer of the graft 110 now has a declotted inner surface 150. These steps can repeated to remove consecutive innermost second layers from the graft after undesirable clotting is formed therealong. With this device and method of use thereof, subsequent inner layers can be independently removed from the graft to control clot formation along the graft while surgically interconnected between two vessels. Thus, graft declotting can be minimized to lengthen the period of implantation of the graft so the surgical introduction of replacement grafts can be delayed.

Figure 8:
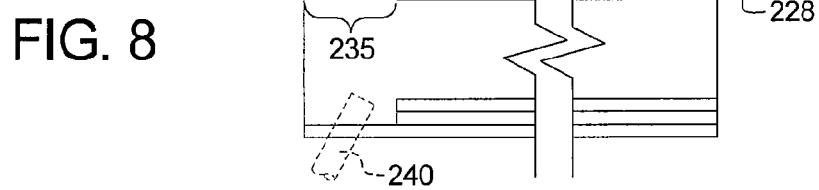
FIG. 8 is a cross-sectional view of another example of a graft.
Figure 9:
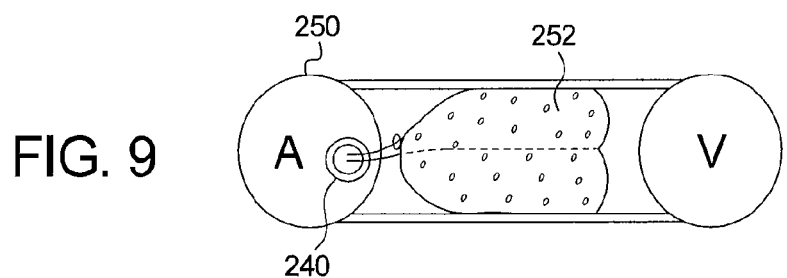
FIG. 9 illustrates an example method of removal of a second inner layer from a graft interconnected between a first vessel and a second vessel, from within the first vessel.

FIG. 8 illustrates another example graft 220. The second layer 222 of the graft 220 is longitudinally offset relative to the first layer 224. To this end, at least one of the first and second ends 226, 228 of the second layer 222, e.g., the second end 228, is closer to an adjacent end 230 of the first layer 224 than the other of the first and second ends, e.g., the first end 226, of the second layer. It is contemplated that the second end may be spaced away from the end 230 by a distance smaller than the distance 235 between the second end 226 and the opposite end 238 of the first layer. The distance 235 is sized to permit an access catheter 240 (dashed lines) to extend through the graft wall in a region external to the second layer. This arrangement may prevent any risk from compromising the second layer during the puncturing process. It is further contemplated that the access catheter 240 can be extended through one of the vessels, shown as the first vessel 250, rather than through the wall of the graft, as shown in FIG. 9. This arrangement may prevent any risk from compromising the second layer or the first layer of the graft during the puncturing process. Both of these arrangements permit the sack 252 to be retracted into the access catheter one end at a time.

It can be appreciated by those skilled in the art that specific features of each embodiment of the grafts are interchangeable among the embodiments, even where no references to the specific features are made.

Drawings in the figures illustrating various embodiments are not necessarily to scale. Some drawings may have certain details magnified for emphasis, and any different numbers or proportions of parts should not be read as limiting, unless so-designated in the present disclosure. Those of skill in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

I claim:

1. A hemodialysis graft comprising:
a graft body having a first end configured to be coupled to a first body vessel, a second end configured to be coupled to a second body vessel, and a wall to define a passageway formed in the graft body, extending between the first and second ends, the wall comprising a plurality of tubular layers,
wherein the plurality of tubular layers comprises a first layer and one or more second layers disposed radially inward relative to the first layer, the first layer and each second layer having a first end and a second end, wherein the first end and the second end of the first layer and each second layer are open to allow passage of a fluid through the passageway between the first body vessel and the second body vessel,
wherein the first layer and the one or more second layers are disposed in an abutting relationship such that no gaps exist between the first layer and the one or more second layers in the wall of the graft body, and
wherein the second layer is capable of being removed from the graft body from within the passageway of the graft body.

2. The graft of claim 1, wherein the first and second ends of the second layer comprise a flexible member, wherein in response to pulling the flexible member, the first and second ends gather radially inward away from a layer adjacent to said second layer.

3. The graft of claim 2, wherein the flexible member has a threaded configuration with said second layer.

4. The graft of claim 3, wherein the flexible member comprises a loop segment.

5. The graft of claim 4, wherein the flexible member comprises a first end and a second end, the first end comprising the loop segment, and the second end comprising an enlarged end.

6. The graft of claim 4, wherein the loop segment of the flexible member of a first of the second layers is circumferentially offset from the loop segment of the flexible member of a second of the second layers, wherein the second of the second tubular layers is adjacent to the first of the second layers.

7. The graft of claim 1, wherein the second layer is attached to a layer adjacent to said second layer.

8. The graft of claim 7, further comprising a continuous layer of adhesive disposed along an entire length of a surface between said second layer and the layer adjacent to said second layer.

9. The graft of claim 1, wherein the second layer is longitudinally offset relative to the first layer such that one of the first and second ends of the second layer is closer to an adjacent end of the first layer than the other of the first and second ends of the second layer.

10. A graft layer retrieval system comprising:
a graft body having a first end configured to be coupled to a first body vessel, a second end configured to be coupled to a first body vessel, and a wall to define a passageway formed in the graft body, extending between the first and second ends, the wall comprising a plurality of tubular layers, wherein the plurality of tubular layers comprises a first layer and one or more second layers disposed radially inward relative to the first layer, wherein the first layer and the one or more second layers are disposed in an abutting relationship such that no gaps exist between the first layer and the one or more second layers in the wall of the graft body, the first layer and each second layer having a first end and a second end, wherein the first end and the second end of the first layer and each second layer are open to allow passage of a fluid through the passageway between the first body vessel and the second body vessel, and a flexible member coupled to at least one of the first and second ends of the second layer; and a grasper having an end configured to removably attach with the flexible member, wherein in response to withdrawal of the grasper subsequent to attachment with the flexible member, the corresponding end of the second layer gathers radially inward away from a layer adjacent to said second layer from within the passageway of the graft body.

11. The system of claim 10, wherein the first end of the second layer has a first flexible member, and the second end of the second layer has a second flexible member.

12. The system of claim 10, wherein the second layer is capable of being removed from the graft body during withdrawal of the grasper.

13. The system of claim 10, wherein the second layer comprises a plurality of openings formed therein, and the flexible member is threaded through the openings so that when tension is applied to the flexible member, the corresponding end is cinched.

14. The system of claim 13, wherein the flexible member comprises a loop segment, and the end of the grasper is configured to engage with the loop segment.

15. The system of claim 14, wherein the flexible member comprises a first end and a second end, the first end comprising the loop segment, and the second end comprising an end sized larger than the openings.

16. The system of claim 14, wherein the loop segment of the flexible member of a first of the second layers is circumferentially offset from the loop segment of the flexible member of a second of the second layers, wherein the second of the second tubular layers is adjacent to the first of the second layers.

17. A method of declotting a graft comprising:

providing a graft interconnected between first and second body vessels, the graft comprising a graft body having a first end coupled to the first body vessel, a second end coupled to a second body vessel, and a wall to define a passageway between the first body vessel and the second body vessel formed in the graft body, extending between the first and second ends, the wall comprising a plurality of tubular layers, wherein the plurality of tubular layers comprises a first layer and one or more second layers disposed radially inward relative to the first layer, wherein the first layer and the one or more second layers are disposed in an abutting relationship such that no gaps exist between the first layer and the one or more second layers in the wall of the graft body, each second layer having a first end associated with the first end of the graft body and a second end associated with the second end of the graft body, enclosing the first end of the second layer, wherein the second layer is the innermost layer of the graft body;

enclosing the second end of the second layer; and removing the second layer after the enclosing steps from the graft body from within the passageway of the graft body, wherein the graft body comprising the first layer remains interconnected between the first and second body vessels after the second layer is removed.

18. The method of claim 17, wherein each enclosing step comprises:

introducing a grasper within the passageway of the graft body;

attaching the grasper to a flexible member coupled to the second layer; and withdrawing the grasper to apply tension to the flexible member so that the respective ends are enclosed.

19. The method of claim 18, wherein each enclosing step comprises:

introducing a grasper within the passageway of the graft body external to the second layer;

attaching the grasper to a flexible member coupled to the second layer; and withdrawing the grasper to apply tension to the flexible member so that the respective ends are enclosed.

20. The method of claim 17, wherein each enclosing step comprises:

introducing a grasper within one of the vessels;

attaching the grasper to a flexible member coupled to the second layer; and withdrawing the grasper to apply tension to the flexible member so that the respective ends are enclosed.

* * * * *